United States Patent [19]

Keen et al.

[11] Patent Number: 4,571,440

[45] Date of Patent: Feb. 18, 1986

[54] CONTINUOUS PROCESS FOR THE PRODUCTION OF ALKYLENE GLYCOL IN THE PRESENCE OF ORGANOMETALATE

[75] Inventors: Brian T. Keen; John H. Robson, both of Charleston, W. Va.

[73] Assignee: Union Carbide Corporation, Danbury, Conn.

[21] Appl. No.: 663,827

[22] Filed: Oct. 23, 1984

Related U.S. Application Data

[63] Continuation of Ser. No. 594,266, Mar. 28, 1984, abandoned.

[51] Int. Cl.$^4$ .................... C07C 29/86; C07C 31/20; C07C 33/26; C07C 35/14
[52] U.S. Cl. .................... 568/872; 568/810; 568/811; 568/833; 568/857; 568/867
[58] Field of Search ............ 568/867, 872, 833, 810, 568/811, 857

[56] References Cited

U.S. PATENT DOCUMENTS

| 4,160,116 | 7/1979 | Mieno et al. | 568/867 |
| 4,277,632 | 7/1981 | Kumazawa et al. | 568/811 |
| 4,283,580 | 8/1981 | Odanaka et al. | 568/811 |
| 4,434,140 | 2/1984 | Hubred et al. | 423/54 |

FOREIGN PATENT DOCUMENTS

| 73035 | 6/1981 | Japan | 568/867 |
| 1177877 | 1/1970 | United Kingdom | 568/867 |
| 2098985 | 12/1982 | United Kingdom | 568/867 |

Primary Examiner—J. E. Evans
Attorney, Agent, or Firm—Steven T. Trinker

[57] ABSTRACT

A continuous process for making alkylene glycols by the hydrolysis of alkylene oxides in the presence of selectivity-enhancing organometalate wherein the alkylene glycol-containing hydrolysis product contains organometalate comprises recovering organometalate by extraction with a water-immiscible solvent, separating the resulting organometalate-containing solvent into an organometalate-lean stream for reuse in the extraction and an organometalate-rich stream for reuse in the hydrolysis.

24 Claims, 4 Drawing Figures

4,571,440

CONTINUOUS PROCESS FOR THE PRODUCTION OF ALKYLENE GLYCOL IN THE PRESENCE OF ORGANOMETALATE

This application is a continuation of application Ser. No. 594,266, filed 3/28/84, now abandoned.

This invention relates to continuous processes for the production of alkylene glycols, particularly monoalkylene glycols, from alkylene oxides and water in the presence of a metalate anion-containing material. Advantageously, the processes of this invention enable the recovery and reuse of the metalate anion in a commercially-attractive manner and without undue deterioration of the metalate anion.

INTRODUCTION TO THE HYDROLYSIS OF ALKYLENE OXIDE USING METALATE ANION

Commercial processes for the preparation of alkylene glycols, for example, ethylene glycol, propylene glycol and butylene glycol, involve the liquid-phase hydration of the corresponding alkylene oxide in the presence of a large molar excess of water (see, for example, Kirk-Othmer, *Encyclopedia of Chemical Technology*, Vol. 11, Third Edition, page 939 (1980)). The hydrolysis reaction is typically conducted at moderate temperatures, e.g., about 100° C. to about 200° C., with water being provided to the reaction zone in excess of 15 moles per mole of alkylene oxide. The primary by-products of the hydrolysis reaction are di- and polyglycols, e.g., dialkylene glycol, trialkylene glycol and tetra-alkylene glycol. The formation of the di- and polyglycols is believed to be primarily due to the reaction of alkylene oxide with alkylene glycol. As alkylene oxides are generally more reactive with alkylene glycols than they are with water, the large excesses of water are employed in order to favor the reaction with water and thereby obtain a commercially-attractive selectivity to the monoglycol product.

Since the alkylene glycols must be recovered from the hydrolysis reaction mixtures, the large excess of water can result in an energy intensive procedure. Typically, the water is removed by evaporation to leave an alkylene glycol-containing residue which is purified by distillation. Hence, a reduction in the amount of water employed while maintaining, or enhancing, selectivity toward the monoglycol product could be beneficial from the standpoint of energy efficiency.

Not only is the monoglycol product often the desired product for the hydrolysis of alkylene oxides but also many of the applications for monoglycols are demanding in the quality of the monoglycol product. For instance, monoethylene glycol is used in the preparation of polyesters (polyethylene terephthalate) and must meet rigid standards so as not to adversely affect the properties of the finished polyesters, e.g., fiber or film. Typical polyester grade monoethylene glycol must meet the specifications set forth in Table I:

TABLE I

| Representative Polyester Grade Specifications | |
|---|---|
| Specific Gravity (20/20° C.) | 1.1151–1.1156 |
| Distillation 760 mm | |
| Ibp, °C. min. | 196 |
| Dp, °C. max. | 200 |
| Acidity, % by wt., as HAc max. acid | 0.005 |
| | Wavelength (mu) / Transmittance (%, min.) |

TABLE I-continued

| Representative Polyester Grade Specifications | |
|---|---|
| UV Transmittances | 220 / 70 |
| | 275 / 90 |
| | 350 / 98 |
| Iron, ppm max. | 0.07 |
| Chlorides | none by test |
| Diethylene glycol, % by wt., max. | 0.08 |
| Water, % by wt., max. | 0.08 |
| Water solubility at 25° C. | miscible, all proportions |
| Ash, gm/100 ml, max. | 0.005 |
| Color, Pt-Co. max. | 5 |
| Odor | mild, practically none |
| Suspended matter | substantially free |

Accordingly, interest exists in assuring that the alkylene glycol product from the hydrolysis process can be readily defined to obtain the desired, high quality product. Any effort to enhance the yield of monoalkylene glycol, e.g., by the use of catalysts, is also viewed from the standpoint of the effect on the quality of the hydrolysis and any additional costs involved in refining the monoalkylene glycol to meet any demanding specifications for the product.

Previously, numerous catalysts have been proposed to enhance the selectivity of the hydrolysis reaction to monoalkylene glycol.

For example, U.S. Pat. No. 4,277,632, issued July 7, 1981, discloses a process for the production of alkylene glycols by the hydrolysis of alkylene oxides in the presence of a catalyst of at least one member selected from the group consisting of molybdenum and tungsten. The patent discloses that the catalyst may be metallic molybdenum or metallic tungsten, or inorganic or organic compounds thereof, such as oxides, acids, halides, phosphorous compounds, polyacids, alkali metal and alkaline earth metal, ammonium salts and heavy metal salts of acids and polyacids, and organic acid salts. An objective of the disclosed process is stated to be the hydrolysis of alkylene oxides wherein water is present in about one to five times the stoichiometric value without forming appreciable amounts of by-products such as the polyglycols. The reaction may be carried out in the presence of carbon dioxide; however, when the reaction is carried out in the presence of nitrogen, air, etc., the patentees state that the pH of the reaction mixture should be adjusted to a value in the range of 5 to 10. Japanese Kokai No. JA 54/128,507, published Oct. 5, 1979, discloses a process for the production of alkylene glycols from alkylene oxides and water using metallic tungsten and/or tungsten compounds.

Japanese Kokai No. JA 56/073,035, published June 17, 1981, discloses a process for the hydrolysis of alkylene oxide under a carbon dioxide atmosphere in the presence of a catalyst consisting of a compound containing at least one element selected from the group of titanium, zirconium, vanadium, niobium, tantalum and chromium. The compounds include the oxides, sulfides, acids, halides, phosphorous compounds, polyacids, alkali metal salts of acids and polyacids, ammonium salts of acids and polyacids, and heavy metal salts of acids.

Japanese Kokai No. JA 56/073,036, published June 17, 1981, discloses a process for the hydrolysis of alkylene oxide under a carbon dioxide atmosphere in the presence of a catalyst consisting of a compound containing at least one element selected from a group comprising aluminum, silicon, germanium, tin, lead, iron, cobalt and nickel.

U.S. patent application Ser. Nos. 428,815, filed Sept. 30, 1982, (now abandoned) and 530,235, filed Sept. 8, 1983, of J. H. Robson and G. E. Keller, disclose the production of monoalkylene glycols with high selectivity by the reaction of a vicinal alkylene oxide with water in the presence of a water-soluble vanadate. Hence, lower water to alkylene oxide ratios can be employed using the disclosed process with attractive selectivities to the monoglycol products. The counter ion to the vanadate is selected to provide a water-soluble vanadate salt under the reaction conditions employed and alkali metals, alkaline earth metals, quaternary ammonium, ammonium, copper, zinc, and iron are suggested cations. It is also disclosed that the vanadate may be introduced into the reaction system in the salt form or on a support such as silica, alumina, zeolites and clay. Since the vanadate ion is water-soluble, it can be lost from the reaction system and means must be provided to recover it from the effluent from the reaction zone.

Selectivity-enhancing metalate anions in association with organic-containing cations or electropositive complexing sites (herein referred to as organometalates) are proposed for use in the hydrolysis of alkylene oxides. Copending U.S. patent application Ser. No. (D-13,943), filed on even date herewith, of J. R. Briggs and J. H. Robson, is directed to processes for the hydrolysis of alkylene oxides in a reaction menstruum comprising two liquid phases, an aqueous phase and a substantially water-insoluble phase in which the concentration of a selectivity-enhancing metalate anion-containing material (which may be an organometalate) is greater in the water-insoluble phase than in the aqueous phase. Advantageously, the alkylene glycol product is preferentially soluble in the aqueous phase and the recovery of the metalate anion-containing material from the product is facilitated by the ability to use phase separation.

Copending U.S. patent application Ser. No. (D-13,955), filed on even date herewith, of J. R. Briggs, G. L. O'Connor, and J. H. Robson, is directed to processes for the hydrolysis of alkylene oxides in which alkylene oxide and a selectivity enhancing, dissociatable metalate anion (which may be an organometalate) are contacted in the relative absence of water under conditions sufficient to associate at least a portion of the alkylene oxide with the metalate anion and then the associated material is contacted with with water to form alkylene glycol. In embodiments of the invention, virtually all the produced alkylene glycol is monoalkylene glycol.

Copending U.S. patent application Ser. No. (D-13,947), filed on even date herewith, of R. D. Best, J. A. Collier, B. T. Keen and J. H. Robson, is directed to processes for the hydrolysis of alkylene oxide in the presence of selectivity-enhancing metalate anion which is in association with electropositive complexing sites on a solid support. Often, the electrocomplexing sites contain hydrocarbyl moieties and are thus encompassed within the group of organometalates. Because the metalate anion is in association with a complexing site on a solid, the recovery of metalate anion from glycol product can be effected by phase separation. Readily available solids include anion exchange resins.

U.S. patent applications Ser. Nos. 530,235; (D-13943); (D-13955); and (D-13947) are herein incorporated by reference.

In order to provide a commercially-attractive process for making alkylene glycols in the presence of selectivity enhancing metalate anion, it is thought to be necessary that the process be operable on a continuous basis. Further, the metalate anion should be recoverable in a form suitable for reuse in the hydrolysis reaction for purposes of economy. The alkylene glycol product should also be sufficiently free of the metalate anion that it provides commercially-available products such as polyester grade ethylene glycol.

However, difficulties have been noted in recovering metalate anion from alkylene glycol product. In particular, the metalate anion is subject to degradation, e.g., by reduction, thereby rendering the metalate anion unsuitable for reuse.

Japanese Kokai No. 56/92228, published July 25, 1981, and Kokai No. 56/118024, published Sept. 16, 1981, disclose processes for producing highly pure alkylene glycols. Kokai No. 56/92228 discloses a process in which alkylene oxide, water and gaseous carbon dioxide are reacted in the presence of a catalyst containing molybdenum and/or tungsten (potassium molybdate was exemplified). An additive such as compounds of alkali metals, compounds of alkaline earth metals, quaternary ammonium salt and quaternary phosphonium salts (potassium iodide is specifically exemplified) may be employed. Carbon dioxide is stripped from the alkylene glycol containing liquid, and then alkylene glycols are stripped to provide a bottom residue containing the catalyst. According to the disclosure, it is essential that the water content of the bottom residue be maintained at a concentration of at least 0.1 weight percent, preferably at least 1 weight percent, particularly 1 to 100 weight percent based on the catalyst. It is noted that if the bottom residue has a water content of less than 0.1 weight percent based on the catalyst and is recycled to the reactor, the yield of monoalkylene glycol is reduced. In the final step, the overhead from the previous stripping zone is distilled to separate water from the alkylene glycol product.

The disclosure of Kokai No. 56/118024 is somewhat similar in that a stripping operation is used to recover the catalyst and the bottoms residue must contain water. The process differs in that no carbon dioxide or additive is necessarily employed in the reaction zone, but the reactor is maintained at a pH of 5 to 10, and the carbon dioxide stripping step is not conducted.

Not only is the effectiveness of the catalyst potentially adversely affected if sufficient water is not present in the bottoms residue according to these Kokais, but, also, a portion of the alkylene glycol becomes oxidized and off-color and is of poor quality.

Although the Kokais represent that the processes can provide highly pure alkylene glycols, certain disadvantages exist such as the need to carefully monitor the amount of water in the bottoms residue to assure that poor quality alkylene glycol is not produced. More significantly, the processes are energy intensive in that the alkylene glycol product and water (since it is lower boiling than alkylene glycols) must be removed as the vapor phase from the catalyst-containing bottoms. Moreover, the temperatures required to accomplish this separation at feasible vacuum conditions exacerbate the risk of degradation of the catalyst.

OVERVIEW OF THE INVENTION

The continuous processes of this invention can enable the recovery of selectivity enhancing metalate anion and its reuse in the process with advantageous selectivities to monoalkylene glycol being maintained. Moreover, the alkylene glycol product can be of desirable quality for commercial processes. Further, the processes enable the recovery of the metalate anion in an attractive integrated manner, particularly from an energy standpoint.

In accordance with the processes of this invention, alkylene oxide and water are provided to a reaction zone containing selectivity-enhancing amounts of metalate anion provided as an organometalate having an organic-containing cation and a metalate anion. The reaction zone is maintained under conditions sufficient to form an aqueous solution of alkylene glycol wherein the aqueous solution also contains organometalate. At least a portion of this aqueous solution is withdrawn from the reaction zone and contacted in an extraction zone with a water-immiscible solvent phase in which organometalate is preferentially soluble as compared to water to form an organometalate-rich, solvent phase. The aqueous solution having a reduced content of organometalate and the organometalate-rich solvent phase from the extraction zone are separated by phase separation to form an aqueous glycol-containing stream and a solvent-containing stream. At least a portion of the solvent-containing stream is separated into an organometalate-lean stream containing water-immiscible solvent and into an organometalate-rich stream. At least a portion of the organometalate-lean stream is introduced into the extraction zone to form at least a portion of the water-immiscible solvent phase therein and at least a portion of the organometalate-rich stream is introduced into the reaction zone to form at least a portion of the organometalate therein.

Since the processes of this invention employ as the selectivity-enhancing metalate anion-containing material an organometalate having an organic-containing cation and a metalate anion, the recovery of the metalate anion from the aqueous, glycol-containing solution can be conducted by extraction thereby avoiding the energy required to separate by distillation the alkylene glycol product from the metalate anion-containing material. Moreover, the metalate anion need not be subjected to conditions that promote the degradation of the anion or result in discoloration or other deterioration of the alkylene glycol product. Advantageously, the process can be readily integrated into the hydrolysis system to provide a commercially-attractive operation from both the standpoints of the ability to recover and reuse the metalate anion and the relatively small energy requirements.

In an aspect of the invention, the water-immiscible solvent has a normal boiling point below that of alkylene glycol, frequently below about 150° C., and preferably below about 100° C. Consequently, the separation of the solvent and organometalate can be effected by vapor-liquid separation at relatively mild conditions, including flash evaporation. With the lower boiling solvents, any entrained alkylene glycol and, in some instances, water, will be be retained in the organometalate-containing liquid phase of the separation and can be recycled to the reactor thereby conserving the alkylene glycol values. Accordingly, it is not essential in these instances to carefully effect the organic/aqueous phase separation to obtain an organometalate-rich solvent stream for separation of at least a portion of the solvent from the organometalate.

The processes of this invention are also advantageous in that they are applicable to different techniques for effecting the hydrolysis. These techniques include the use of a water-soluble organometalate in the reaction zone (homogeneous system), the use of an aqueous phase and a substantially water-insoluble, organometalate containing phase in the reaction zone (two phase process), and the sequential process of first contacting the alkylene oxide with organometalate in a zone having a relatively absence of water and then contacting the alkylene oxide-containing material with water to form alkylene glycol (two step process).

DISCUSSION RELATING TO THE REACTANTS

Alkylene oxides which may be used to produce alkylene glycols in the processes of this invention are vicinal alkylene oxides having the general formula:

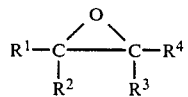

wherein $R^1$, $R^2$, $R^3$ and $R^4$ are the same or different and are hydrogen or hydrocarbyl-containing substituents of 1 to about 20 carbon atoms. Often $R^1$, $R^2$, $R^3$ and $R^4$ are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms. Representative of alkylene oxides are ethylene oxide, propylene oxide, butylene oxide, including isobutylene oxide, 1,2-butylene oxide and 2,3-butylene oxide, pentylene oxide, styrene oxide, cyclohexene oxide and the like. Preferably, the alkylene oxide is an aliphatic alkylene oxide having 2 or 3 carbon atoms, i.e., ethylene oxide and propylene oxide.

Alkylene oxides are well known, as is their preparation. For example, alkylene oxide can be prepared by reacting an olefin with an organohydroperoxide in the presence of a catalyst or by the partial oxidation of an alkene (especially ethylene) with a molecular oxygen-containing gas in the presence of a silver catalyst.

Water (as the liquid or steam) is also employed as a reagent for the formation of the corresponding alkylene glycol. Usually the water is of sufficient purity to provide a suitable quality alkylene glycol product. Liquid water may be distilled or demineralized, for example, by ion exchange treatment.

The metalate anions are characterized by an anionic structure containing at least one metal atom and at least one oxygen ligand conventionally characterized as double-bonded oxygen atom.

The metalate anions which may be useful in the processes of this invention comprise a polyvalent metal having a positive oxidation state, often an oxidation state of at least +3, say, +4 to +6 or +7, and may be a transition metal. The metalate anions may be illustrated by the following formula:

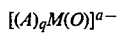

wherein a− is the negative charge of the anion which is often −1 to −4, A is one or more substituents to fill the remaining valencies (q) of M and may be, for instance, double-bonded oxygen; an organic radical such as an alkyl, alkoxy, acyl, aryl, amino, phosphine, etc., usually of 1 to about 12 carbon atoms; halogen (e.g., chlorine, fluorine, iodine); —O— or —S— wherein the remaining valency of the oxygen atom is in free ionic form or is bonded to a metal atom (as in a bimetal or polymetal-containing metalate) or cation. Most commonly A is —O— or =O. Even when the A in the starting organometalate is other than —O—, e.g., chlorine, it is possible that the original substituent becomes replaced by —O— in the course of the process.

Particularly preferred metals for the metalate anions include the metals in groups Vb and VIb of the periodic chart such as vanadium, molybdenum and tungsten, although other metals such as rhenium and germanium may also find application. Representative metalate anions which are especially useful include molybdate, tungstate, metavanadate, hydrogen pyrovanadate and pyrovanadate; although because of the complex chemistry associated with many metalate anions, the precise structure of the operative specie or species may be different. Frequently the metalate anion comprises at least one anion conventionally characterized by the formulae $[MoO_4]^{2-}$, $[VO_3]^-$, $[V_2O_7H]^{3-}$, $[V_2O_7]^{4-}$, and $[WO_4]^{2-}$; however, it is recognized that the chemistry of these metalate anions, particularly the vanadates, is complex, and the exact chemical formula under the conditions of the process may prove to be different.

Not all metalate anions, including those of vanadium, tungsten and molybdenum, exhibit desired activity with alkylene oxide. For example, it has been observed that paramolybdate and paratungstate anions (as the metalate anion added) appear to exhibit little, if any, activity for enhancing selectivity.

Advantageously, the metal for the metalate anion is selected on the basis of the nucleophilicity and electrophilicity in the anion with respect to alkylene oxide in the environment. For example, the metal as in the metalate often has a nucleophilicity with respect to ethylene oxide greater than that exhibited by rhenium as in rhenate anion under the same conditions. Also, it is frequently the case that the metal as the metalate has an electrophilicity with respect to ethylene oxide greater than that exhibited by vanadium in orthovanadate (as that species) under the same conditions.

A particularly convenient method for approximating nucleophilicity and electrophilicity characteristics of a metal in a metalate anion is by comparing the rate and selectivity to monoethylene glycol under substantially the same hydrolysis conditions but employing an equimolar amount (based on the anion) of the subject metalate anion and the reference anion. For the sake of ease, the cation may be sodium. If the rate and/or selectivity to the monoethylene glycol is less than that provided by the rhenate anion, then the metal as the metalate is probably less nucleophilic than rhenium as in rhenate with respect to ethylene oxide. If the production of diethylene glycol and polyethylene glycol is greater than that provided with orthovanadate, regardless of the rate of formation of ethylene glycols, then the metal as the metalate is probably less electrophilic than orthovanadate with respect to ethylene oxide.

The metalate anions are associated with a cation and are dissociatable from the cation. Although the cations may be substantially insoluble, or have little solubility, in water at reaction conditions, the metalate anion can provide the enhanced selectivity to monoalkylene glycol. However, if the metalate anion is too tightly bound, it will not have the desired activity. Thus, calcium vanadate, which has little solubility in water and retains the metalate anion tightly bound, has not been found to be an acceptable metalate-containing compound. On the other hand, where the cation is, for instance, an essentially insoluble quaternary ammonium moiety, the dissociatable nature of the metalate anion is believed to permit its usefulness to achieve enhanced selectivities to monoalkylene glycol.

In accordance with the invention, the cations render the organometalate preferentially soluble in an organic medium as compared to water. Often, the organometalate will have a greater solubility in a given water-immiscible organic solvent such as toluene than in distilled water at a given temperature, say, 25° C. In some instances, the solubility coefficient is at least about 5 times, say, at least about 20 times, greater in toluene than the solubility in distilled water at 25° C.

Useful organometalates also include those that are substantially insoluble in distilled water, e.g., less than about 50, say, less than 10, grams of the organometalate will dissolve in one liter of water at 25° C. Some organometalates are immiscible with water and some are solid at ambient temperatures, for instance, 25° C., or even at temperatures suitable for the processes of this invention, e.g., about 50° to 250° C.

The organometalate is preferably highly soluble in the water-immiscible solvent. Usually, at 25° C., the organometalate is soluble in toluene in an amount of at least about 50 grams per liter, say, at least 100 grams per liter, and sometimes the organometalate and toluene are miscible in all proportions.

Particularly useful organometalates may be represented by the formula:

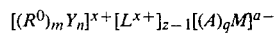

$$[(R^0)_m Y_n]^{x+} [L^{x+}]_{z-1} [(A)_q M]^{a-} \qquad \text{I}$$

wherein $[(R^0)_m Y_n]^{x+}$ is an organo-containing cation having a positive charge of x and Y is a polyvalent element, which is an ionic charge carrying center, $R^0$ is hydrogen or hydrocarbyl-containing substituent with the proviso that the organo-containing cation has at least one $R^0$ which contains a hydrocarbyl substituent, m is the average number of electron pairs shared by Y with the total $R^0$ groups, n is the number of charge carrying centers, wherein m, n and x are related by the equation $x = n(V-m)$ in which V is the average functional oxidation state of Y wherein each electron pair used by each Y in bonding to $R^0$ is given the value of 1 and the functional oxidation state of Y is the sum of the electron pairs bonding to $R^0$ and x/n, wherein x is an integer of 1 or 2; wherein L is a cation which has a positive charge of x' and which may be the same or different from the organo-containing cation, where x' is usually 1 or 2; wherein z is the number of organo-containing cations which is from 1 to 3. Hence, the negative charge, a, of the metalate anion equals the amount of $x + [(z-1)(x')]$.

The hydrocarbyl-containing substituents useful in the organo-containing cation frequently contain at least four carbon atoms, and may be further substituted with moieties that are not reactive with the anion.

L may be any suitable cation and often is another organo-containing cation or a non-organo-containing cation which serves to balance the charge of the anion. L may include alkali metals, alkaline earth metals, copper, zinc, iron, ammonium cations, phosphonium cations, sulfonium cations, and other cations including organic-containing cations, e.g., containing alkyl, alkoxy, acyl, aryl, amino, phosphino, etc., groups of 1 to about 12 carbons.

Suitable cations may include structures represented by the formulae:

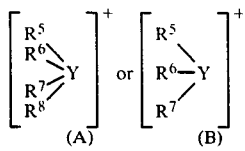

where Y is nitrogen, phosphorous, or arsenic for formula A, or sulfur for formula B, i.e., ammoniums, phosphoniums, arsoniums and sulfoniums, where each of $R^5$, $R^6$, $R^7$ and $R^8$ may be the same or different and may combine to form cyclic structures. Exemplary of each of $R^5$, $R^6$, $R^7$ and $R^8$ are hydrogen and unsubstituted and substituted hydrocarbyls of 1 or more carbon atoms, e.g., to about 70 carbon atoms. Representative cations are disclosed in copending U.S. patent application Ser. No. (D-13956), filed on on even date herewith, of J. R. Briggs and J. H. Robson, herein incorporated by reference.

Other organo-containing cations which may be useful include the bis(hydrocarbyl-phosphine)-iminiums represented by the formula $$[(R_3^9P)_2N]^+$$

wherein each $R^9$ may be the same or different and may be the same as set forth for $R^5$ to $R^8$. Illustrative iniminiums are disclosed in Ser. No. (D-13,956).

Illustrative of the organo-containing cations are tetrahydrocarbyl ammoniums, e.g., tetramethyl ammonium, tetraethyl ammonium, tetra-n-propyl ammonium, tetra-n-butyl ammonium, tetra-isobutyl ammonium, trimethyl butyl ammonium, tetraheptyl ammonium, tetraphenyl ammonium, tetrabenzyl ammonium, tetradodecyl ammonium, tetraoctadecyl ammonium, and the like; trihydrocarbyl ammonium, e.g., trimethyl ammonium, triethyl ammonium, triphenyl ammonium, tridodecyl ammonium, trioctadecyl ammonium, and the like; dihydrocarbyl ammoniums, e.g., dimethyl ammonium, diethyl ammonium, di-n-butyl ammonium, di-n-heptyl ammonium, diphenyl ammonium, dibenzyl ammonium, didodecyl ammonium, dioctadecyl ammonium, and the like; hydrocarbyl ammoniums, e.g., methyl ammonium, n-butyl ammonium, dodecyl ammonium, octadecyl ammonium, phenyl ammonium, benzyl ammonium, and the like; tetrahydrocarbyl phosphoniums, e.g., tetramethyl phosphonium, tetraethyl phosphonium, tetra-n-propyl phosphonium, tetra-n-butyl phosphonium, tetra-isobutyl phosphonium, trimethyl butyl phosphonium, tetraheptyl phosphonium, tetraphenyl phosphonium, tetrabenzyl phosphonium, tetradodecyl phosphonium, tetraoctadecyl phosphonium, and the like; trihydrocarbyl phosphonium, e.g., trimethyl phosphonium, triethyl phosphonium, triphenyl phosphonium, tridodecyl phosphonium, trioctadecyl phosphonium, and the like; dihydrocarbyl phosphoniums, e.g., dimethyl phosphonium, diethyl phosphonium, di-n-butyl phosphonium, di-n-heptyl phosphonium, diphenyl phosphonium, dibenzyl phosphonium, didodecyl phosphonium, dioctadecyl phosphonium, and the like; hydrocarbyl phosphoniums, e.g., methyl phosphonium, n-butyl phosphonium, dodecyl phosphonium, octadecyl phosphonium; phenyl phosphonium, benzyl phosphonium, and the like; bis(-hydrocarbyl-phosphine)iminiums such as bis(triphenyl-phosphine)iminium, bis(tribenzyl-phosphine)iminium, bis(trimethyl-phosphine)iminium, bis(tridodecyl-phosphine)-iminium, and the like; quaternized diamines such as N,N'-bis(trimethyl)propylene diamine, N,N'-bis(triphenyl)propylene diamine, N,N'-bis(trioctadecyl)propylene diamine; and quaternized diphosphines such as P,P'-bis(trimethyl)propylene diphosphine, and the like.

The metalate anion may be provided to the reaction mixture as a metalate anion or in a form which is converted to the desired metalate anion by subsequent chemical reaction. Hence, halide, sulfide, or the like, metal-containing compounds may be employed as the precursor to the desired metalate anion. Some of these precursor compounds may be converted to metalates during the hydrolysis reaction.

The water-immiscible solvents used for the extraction of the organometalate are generally alkyl, cycloalkyl and aromatic-containing solvents such as halogenated alkyl, cycloalkyls and aromatics such as cyclopentane, cylcohexane, methylcyclohexane, cycloheptane, benzene, toluene, xylene, naphthene, carbon disulfide, dichloromethane, 1,1,2-trichloroethane, carbon tetrachloride and the like. Silicone oils and mineral oils may also find application.

The solvent may be denser or less dense than water. Often, the density of the solvent is sufficiently different from the aqueous glycol-containing stream in the extraction zone to facilitate phase separation. For example, the densities may differ by at least about 0.05, say, at least about 0.1, gram per milliliter under the conditions of the extraction zone.

The selection of the solvent may be influenced not only by its ability to extract the organometalate but also whether it will be employed in the reaction zone, its normal boiling point, and inertness to the organometalate and alkylene glycol. Most preferably, the alkylene glycol is preferentially soluble in the water as compared to the solvent at 25° C., e.g., it is often at least 5 or 10 times, say, at least 20 or 50, times more soluble in water than the solvent. Particularly useful solvents are those which do not adversely affect the quality of the monoalkylene glycol if present in trace amounts.

HYDROLYSIS REACTION PROCESSES

As stated above, the processes of this invention can use various types of hydrolysis reaction systems. Because of the potential for interaction throughout the process, the type of hydrolysis reaction system that is used will necessarily influence the details of the remaining features of the process.

In general, the hydrolysis reaction involves providing alkylene oxide, water and organometalate to a reaction zone. The relative amounts of these components and the presence of one or more solvents or adjuvants can vary widely depending upon the sought selectivity to monoalkylene glycol, the sought hydrolysis ratio, and the type of hydrolysis reaction system used. Hence, the optimal operating parameters will vary. However, the general considerations for the processes will be common to many of the hydrolysis reaction systems. The following discussion provides a guide to conditions which are often encountered in the processes of this invention.

Usually, the amount of the aqueous phase is selected in respect to the amount of alkylene oxide employed in the process since it is a reactant and must be separated from the alkylene glycol products. The unreacted water serves as a heat sink to assist in maintaining desired temperatures during the exothermic hydrolysis reaction. Its importance, however, can vary. With homogeneous processes, it can be a significant consideration. When employing a two-phase process, the solvent present also serves as a heat sink and will therefore reduce the need for water as a heat sink. In two-step processes, the interaction between the alkylene oxide and metalate is believed to form an associated moiety. (For all purposes herein, the associated moiety will be encompassed within the term alkylene oxide.) When this associated moiety is contacted with water, alkylene glycol is produced but the heat produced is considerably less than that produced by the reaction of alkylene oxide with water. Consequently, in the two-step processes, the role of water as a heat sink may be relatively minor.

The mole ratio of water (which under the conditions of the process may be provided in liquid form or steam) to alkylene oxide is often in the range of about 0.5:1 to 50:1, and preferably, the amount of water employed is at least sufficient on a stoichiometric basis to react with all the alkylene oxide provided, e.g., the mole ratio is at least 1:1 up to, say, about 40:1 or 50:1, say, about 1:1 to 20:1.

It is believed that the hydrolysis reaction in the processes of this invention can proceed by at least two routes, one involving the selectivity-enhancing metalate and the other being the conventional route. Thus, the processes of this invention are capable of producing dialkylene glycol and higher glycols. Hence, the lower the ratio of water to alkylene glycol, all other factors remaining the same, the greater the amount of these dialkylene and higher glycols that will be produced. This provides a degree of flexibility in operating processes of the invention to provide a desired amount of these higher glycols but an amount less than would be obtained in a conventional process. In most instances, the mole ratio is in the range of about 3:1 to 10:1; however, for two-step processes, lower mole ratios are frequently preferred, say, about 1:1 to 5:1.

Another factor affecting the degree of selectivity to the monoalkylene glycol is the amount of metalate anion employed. Generally, the greater the amount of metalate anion employed, the higher the selectivity to monoalkylene glycol, all other factors remaining the same. Thus, the mole ratio of metalate anion to alkylene oxide may be up to 5:1 or 10:1 or more. Economics usually dictate that the mole ratio of metalate anion to alkylene oxide will be less than about 2:1. Often, the mole ratio is at least about 0.001:100, say, in the range of about 0.05:100 to 2:1, e.g., about 0.1:100 to 1:1, and most frequently about 1:100 to 0.5:1. In two-step processes, mole ratios of metalate anion to alkylene oxide are often closer to those required for complete association of the alkylene oxide with the metalate anion in order to ensure substantially 100 percent selectivity to the monoalkylene glycol. In processes in which the organometalate is dissolved in the aqueous phase, less organometalate may be required to achieve a given selectivity to monoalkylene glycol than that to obtain the same selectivity when the organometalate is in a separate phase such as in the two-phase processes. It is also possible to use in the reaction zone a solid-containing metalate anion in association therewith. For example, in copending U.S. patent application Ser. No. (D-13947), anion exchange resins are disclosed which have electropositive complexing sites which, among other possibilities, can be quaternary ammonium or quaternary phosphonium moieties that are in association with the metalate anion. When using such solids, the availability of metalate anion sites may be restricted. Thus, greater ratios of metalate anion to alkylene oxide are preferred, say, about 0.01:1 to 20:1, e.g., about 0.05:1 to 15:1.

For purposes of determining the moles of metalate anion present, in respect to anions containing more than one site which is available for association with alkylene oxide, e.g., molybdate and tungstate, the moles shall be calculated based on the number of such sites.

Solvent may also be present during the hydrolysis reaction. In hydrolysis reaction processes such as the two-step process and the two-phase process, a substantially water-insoluble solvent is typically present, and the organometalate is dissolved therein.

The amount of solvent, when employed, can vary widely and is frequently in the range of about 0.1:1 to 10:1 volumes per volume of water. The amount of solvent employed is often determined based upon the solubility of the metalate anion-containing material in the solvent, whether the substantially water-insoluble phase is to be the continuous phase, the desired mass for the dissipation of heat from the exothermic reaction, and the like.

In some instances it may be desirable to use interactive solvents such as 1,2-dimethoxyethane. These solvents are often miscible with water and can be used in many hydrolysis reaction processes and seem to enhance the selectivity to monoalkylene glycol.

The hydrolysis can be conducted under conditions sufficient to effect the hydrolysis and often to maintain the aqueous phase and, if present, substantially water-insoluble phase in liquid form. The temperature, however, should not be so great that the metalate anion-containing moiety is unduly adversely affected. Frequently, the reaction temperature is between about 20° C. and about 220° C. or 250° C., say, between about 50° C. and 200° C., and sometimes between about 80° C. and 180° C. In some cases, the metalate anion-containing material may be subject to degradation at temperatures in excess of, for example, 140° C. or 150° C., and thus lower temperatures would be advantageous even though the rate of reaction decreases with decreasing temperature.

The processes may be conducted at subatmospheric, atmospheric or superatmospheric pressure. For purposes of convenience, the reaction is typically conducted at pressures greater than ambient, e.g., between about 0.1 and 1000 kilograms per square centimeter gauge, and preferably between about 2 and 100 kilograms per square centimeter gauge.

The hydrolysis may be conducted for a time insufficient for complete reaction, but it is generally preferred that when water is provided in amounts sufficient for complete reaction with the alkylene oxide, the reaction is conducted for a period of time sufficient to ensure that substantially all the metalate anion is reacted. The amount of time required to accomplish the substantially complete reaction is determined by the other conditions employed including temperature, amount of reactants present, and the like. The reaction may be carried out for very short periods of time; e.g., fractions of a second, and, if desired, may be carried out for periods of up to hours, e.g. about 0.01 second to 5 hours, preferably about 1 second to 30 minutes.

The alkylene oxide may be a gas under the conditions of the reaction and may be introduced into the liquid medium as a fine dispersion of gas bubbles, but most frequently, the pressure is sufficient to maintain the alkylene oxide in the liquid phase.

The hydrolysis may be conducted in the presence of a gas, which is preferably inert. Gases which may be employed include air, carbon dioxide, nitrogen, argon and the like. Carbon dioxide is often present by the very nature of the process and the source of the alkylene oxide (especially by partial oxidation of ethylene). Frequently, it is desired to maintain the mole ratio of carbon dioxide to alkylene oxide less than 0.1:1, particularly less than 0.05:1, unless it is desired to affect the pH of the reaction menstruum. Carbon dioxide can be used in certain amounts to enhance the selectivity provided by vanadate anion such as disclosed in U.S. patent application Ser. No. (D-14366), filed on even date herewith, of B. T. Keen, herein incorporated by reference.

The pH of the reaction menstruum is frequently maintained relatively neutral, e.g., between about 5 and 11, preferably about 6 to 10.5, and most often the pH is in the range of about 6 to 10. With some metalate anions, such as the vanadates, tungstates and molybdates, the pH of the medium can be determinative of the species present. For example, in strong bases the orthovanadate may predominate, but at neutral conditions metavanadate may exist. In another example, more acidic media promote the formation of polynuclear molybdates which often have less, if any, activity towards forming the associated moiety.

The pH may be maintained within the desired range by the addition of acid or base, or the addition of buffers, as is well known in the art. However, the presence and nature of salts should be considered since the cation may displace the cation for the metalate anion. Mechanisms which have been proposed for maintaining the desired pH in other types of hydrolysis processes include the addition of carbon dioxide or inorganic acids or organic acids such as sulfuric acid, hydrochloric acid and acetic acid. The agents for maintaining the pH value of the reaction menstruum may be added in any convenient manner such as during the reaction, e.g., by purging with carbon dioxide, or by addition to one or more of the reactants prior to introducing the reactants into the reactor.

The maintenance of the pH within the desired ranges can also have a secondary effect of enhancing the stability of the metalate anion.

The reaction vessel or vessels for the hydrolysis reaction will differ depending upon the hydrolysis reaction system used. For instance, with a homogeneous system, the apparatus may be a tank or tube having as a primary design feature providing a sufficient residence time for the reaction. In a two-phase system and some two-step systems, means to provide intimate contact between the aqueous and non-aqueous phases are desirable. Such processes may be conducted in any suitable manner for reactions in menstruum containing more than one phase. For instance, the aqueous phase may provide the continuous phase or the substantially water-insoluble phase may be the continuous phase. In general, it is desired that the discontinuous phase is highly dispersed and is in the form of small bubbles to enhance the interface areas between the phases. For example, the discontinuous phase can have bubble diameters of less than about 2, say, less than about 1, e.g., about 0.01 to 0.5, centimeters. Devices to enhance the dispersion may be employed such as agitators, spargers and the like. The vessels may contain packing, trays and the like to further promote contact. However, in order to obtain an enhanced selectivity to monoalkylene glycol, it is not usually essential to have a dispersed phase. Indeed, the phases may form adjacent layers during conducting the reaction.

The feed, or various components, may be pre-mixed before being introduced into the reactor or the components may be separately introduced into the reaction vessel. For instance, a substantially water-insoluble liquid phase can be admixed with alkylene oxide and introduced into an aqueous phase in the reaction vessel. Alternatively, alkylene oxide may be separately introduced into a reaction vessel containing a substantially water-insoluble liquid phase and an aqueous phase. In any event, the process should be operated such that at least a portion of the alkylene oxide has an opportunity to contact the substantially water-insoluble phase containing the metalate anion-containing material prior to reaction with water.

THE INTEGRATED PROCESSES

For sake of ease of understanding, the processes of this invention will be further described in connection with the drawings, but such reference is not intended to be in limitation of the invention. In the drawings.

Figure 1:
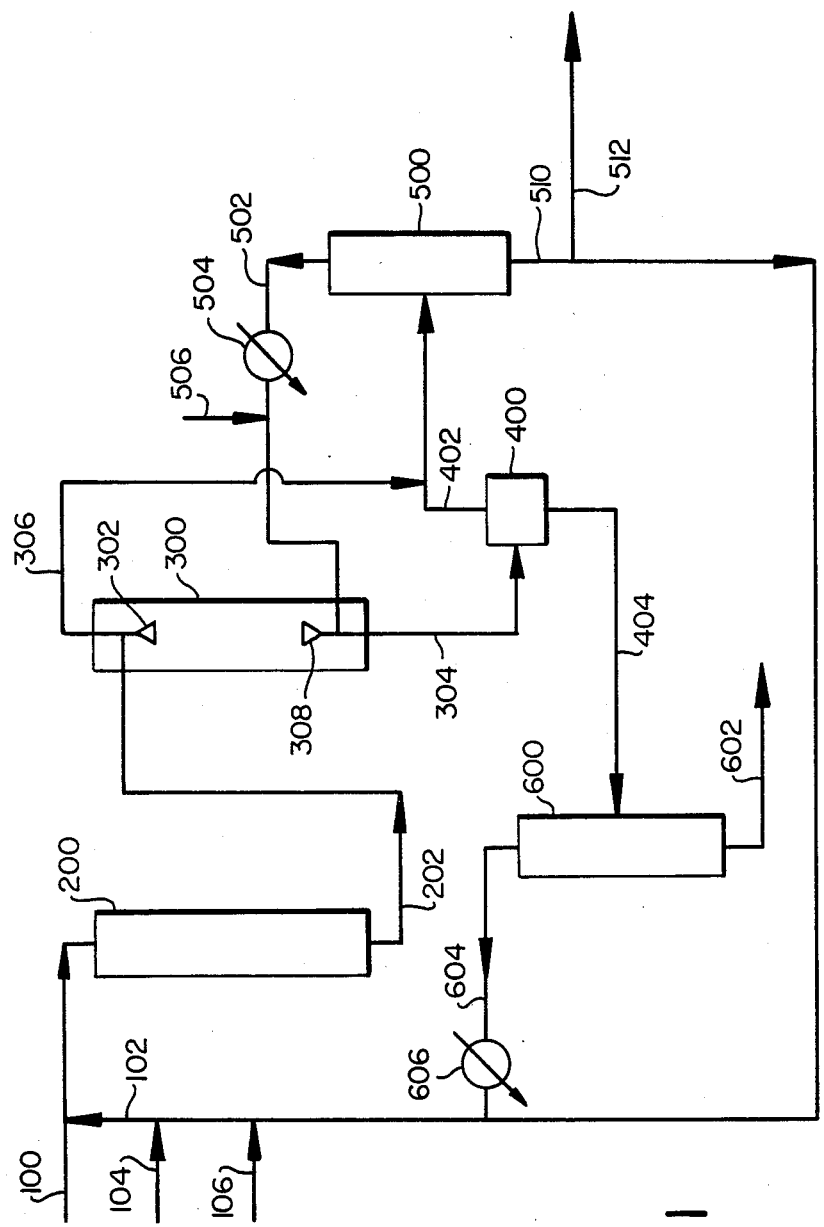
FIG. 1 is a schematic diagram of a process in accordance with this invention using a homogeneous hydrolysis reaction system.

In the drawings, like reference numerals refer to like features. For the sake of simplicity, heat exchangers, pumps, and other such equipment are not depicted. In the drawings, it has been assumed that the solvent is less dense than the aqueous phases, e.g., the solvent is hexane. It is readily apparent that denser solvents can be employed in which event design modifications will be necessary.

With respect to FIG. 1, alkylene oxide is passed via line 100 to hydrolysis reactor 200. Hydrolysis reactor 200 is an adiabatic downflow reactor. The ethylene oxide passing through line 100 is admixed with a water and organometalate solution provided by line 102.

The reaction product from hydrolysis reactor 200 is passed via line 202 to extraction vessel 300. The fluid in line 202 comprises alkylene glycol, water and organometalate. The aqueous solution from line 202 is introduced via distributor 302 in an upper portion of extraction vessel 300. The aqueous solution flows downward and exits extraction vessel 300 at its bottom via line 304. In countercurrent flow in extraction vessel 300 is a water-immiscible solvent.

In the extraction vessel 300, the aqueous phase or the solvent phase may be the continuous phase. Advantageously, the discontinuous phase is highly dispersed throughout the extraction vessel and is in the form of small bubbles to increase the interface area between the phases and thereby promote the extraction of the organometalate. For example, the discontinuous phase can have bubble diameters of less than about 2, say, less than about 1, e.g., about 0.01 to 0.5, centimeters. In order to assure a highly dispersed, discontinuous phase, spargers, agitators, and the like are particularly desirable.

The relative amount of the aqueous phase and the solvent phase in the extraction vessel can vary widely and will depend upon, for instance, the amount of organometalate that is to be extracted and the relative affinity of the organometalate to the solvent. In most instances, the volume ratio of the aqueous solution to the solvent is about 1000:1 to 1:10, say, about 10:1 to 1:2.

The aqueous stream from the extraction vessel preferably contains little organometalate, often, less than about 1000 ppm by weight, preferably, less than about 50 ppm by weight, of the organometalate. The aqueous stream in line 304 is passed to separator 400 which enables any entrained solvent to separate from the aqueous, glycol-containing phase.

The solvent phase from separator 400 is passed via line 402 to distillation column 500.

From the top of the extraction vessel 300 an organometalate-rich solvent phase is withdrawn through line 306 and is passed to distillation column 500 together with the solvent phase in line 402 from the separator 400. At the top of the extraction vessel 300 a zone is provided above distributor 302 to enable some of the entrained aqueous phase to be separated from the solvent phase prior to entering line 306. The organometalate-rich solvent phase will, however, usually contain entrained aqueous phase. The presence of the aqueous, glycol-containing phase in the organometalate stream is generally not deleterious.

In distillation column 500, a separation is made to provide a vaporous water-immiscible solvent overhead which contains substantially no organometalate. Conveniently, distillation column 500 employs a lower pressure than that used in the reactor 200 or extraction vessel 300. Consequently, with solvents having boiling points below that of water, the upper portion of the still may be at temperatures below 120° C., say, below about 100° C., e.g., 50° to 95° C., and the still bottom, even though it is at a higher temperature than the upper portion of the distillation column, may be at a temperature in the range of about 90° to 150° C. The pressure of the distillation column is frequently in the range of about 0.05 to 5, say 0.1 to 1, atmospheres absolute. Accordingly, distillation column 500 can be operated under conditions which do not unduly adversely effect the organometalate.

The overhead from distillation column 500 passes through line 502 and through condenser 504 to provide the water-immiscible solvent in liquid phase and enters extraction vessel 300 through distributor 308. Make-up water-immiscible solvent can also be introduced into the stream passing to the extraction vessel 300 via line 506. Distributor 308 is positioned above the bottom of extraction vessel 300 in order to enable some phase separation of any entrained solvent phase from the aqueous, alkylene glycol containing phase prior to its exit via line 304.

The extraction is conducted under conditions of temperature and pressure sufficient to maintain the aqueous and solvent phases in liquid form. Generally, the temperature of the extraction is in the range of about 0° C. to 220° C., say, about 50° C. to 180° C. Advantageously, for purposes of energy conservation, the extraction is conducted at substantially the same pressure and temperature that was employed in the hydrolysis reaction.

Although a countercurrent-type extraction is depicted, it is equally apparent that any suitable extraction system could be employed including a cocurrent-type extraction system and multiple staged extraction systems. The particular system employed will be selected from the standpoints of equipment cost and degree of recovery of the organometalate. Regardless of the extraction system employed, the weight ratio of organometalate to be removed to water-immiscible solvent is between about 1:10,000 to 1:2, e.g., about 1:100 to 1:10. Typically, the weight ratio of organometalate to water-immiscible solvent exiting extraction vessel 300 is within the range of about 0.01 to 200, say, about 1 to 100 parts per 1000 parts of water-immiscible solvent.

The bottoms from distillation column 500 are passed via line 510 to line 102 for reuse in the hydrolysis reaction. This stream will contain alkylene glycol, water and organometalate as well as some water-immiscible solvent. The amount of water-immiscible solvent present will, of course, depend upon the thoroughness of the distillation. In some instances, it is desired to purge a portion of the bottoms from the system via line 512.

An aqueous, alkylene glycol-containing phase, having a reduced content of the water-immiscible solvent, is recovered via separation vessel 400. Separation vessel 400 may be a decanting vessel wherein sufficient residence time is provided for the solvent phase to form an upper layer, or it may employ mechanical means to assist the separation of the phases such as centrifugation. The aqueous phase from separator 400 passes via line 404 to evaporator 600. In evaporator 600, a substantial portion of the water is evaporated from the alkylene glycol product which remains as the liquid phase and is removed via line 602 for distillation and purification. The water-containing vapor phase is removed from evaporator 600 via line 604 and can be reused in the system by condensing in condenser 606 and combining it with the water returning to reactor 200. Evaporator 600 may be operated in generally the same manner as an evaporator in a conventional alkylene oxide hydrolysis process. It is also evident that instead of evaporator 600, a distillation column could be employed for the separation of the water from the alkylene glycol products.

In order to maintain water balances, make-up water can be provided to the system via line 104 to be passed to the hydrolysis reactor 200, and make-up organometalate may be provided via line 106 to be introduced into reactor 200. It is, of course, possible to pre-mix the make-up water and make-up organometalate as well as to pre-mix one or both of these components with the alkylene oxide provided in line 100.

Figure 2:
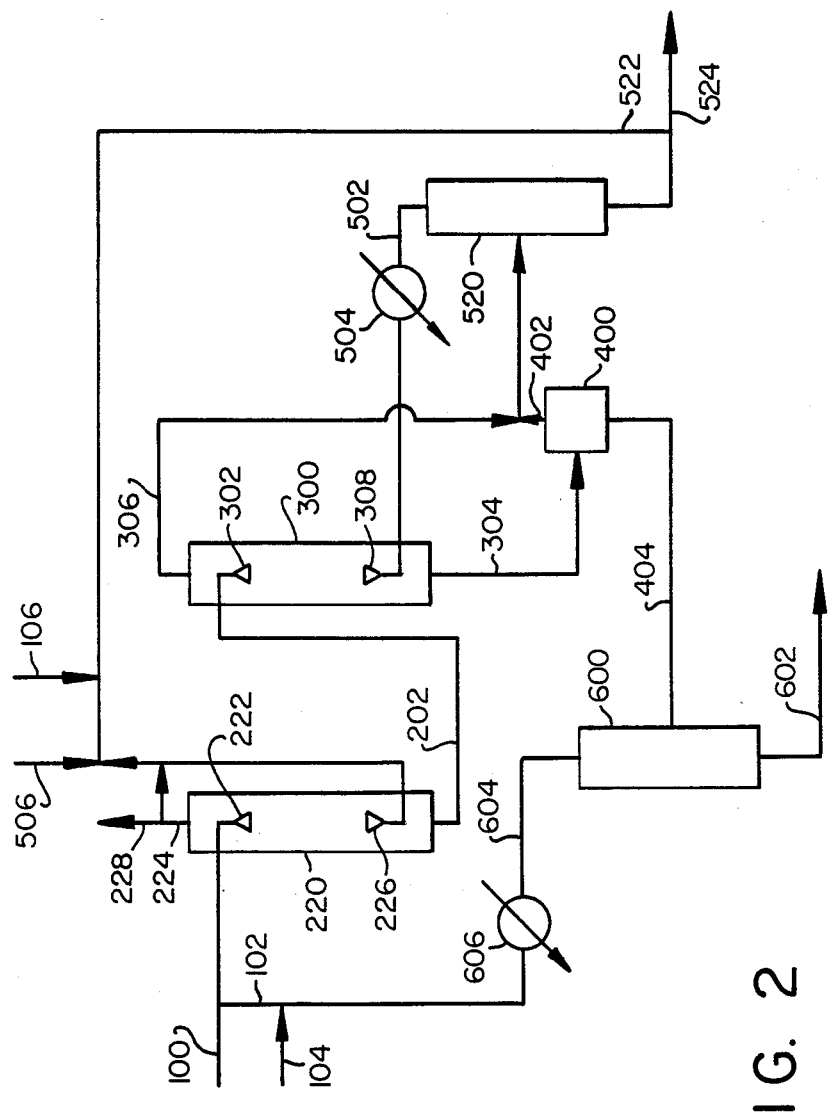
FIG. 2 is a schematic diagram of a process in accordance with this invention using a two-phase hydrolysis reaction system.

In the system depicted in FIG. 2, a two-phase hydrolysis reaction zone is depicted. As depicted in the Figure, a mixture of water and alkylene oxide is fed from line 100 to distributor 222 into an upper portion of reactor 220. Distributor 222 directs the water-containing phase downward whereat it is met by an upward-flowing organometalate-containing solvent phase. A region is provided in reactor 220 above distributor 222 to permit some of the entrained aqueous phase to separate from the solvent phase. The solvent phase, which contains organometalate, is withdrawn from the top of reactor 220 via line 224 and is recycled to a bottom portion of reactor 220 where it is introduced into the reactor via distributor 226. Distributor 226 is positioned above the bottom of the reactor 220 to enable some of the entrained organic phase to separate from the aqueous, alkylene glycol-containing phase. Line 228 enables a purge of the solvent phase from line 224.

Because the depicted system is intended to employ water-immiscible solvent in the reactor 220, there is less need for the water-immiscible solvent to be removed substantially completely from the organometalate as was desired in the system depicted in FIG. 1. Accordingly, flash evaporator 520 is employed instead of distillation column 500. Flash evaporator 520 is operated so that sufficient water-immiscible solvent is obtained in the overhead for use in the extraction. Frequently, flash evaporator 520 is operated so that the bottoms contain a substantial amount of the water-immiscible solvent. Since the hydrolysis reaction is conducted using a two-phase system, water-immiscible solvent will be entrained and carried through the extraction vessel 300 to flash evaporator 520. Thus, the system depicted provides a mechanism for returning the entrained solvent to reactor 220 via line 522. Line 524 is in communication with line 522 and enables a purge stream to be taken. Line 506 provides for make-up water-immiscible solvent. Alternatively, or in addition, make-up solvent could be provided to line 502 and directed to extraction vessel 300. In the depicted system, the make-up organometalate is provided via line 106 to line 522 to be directed to reactor 220.

Figure 3:
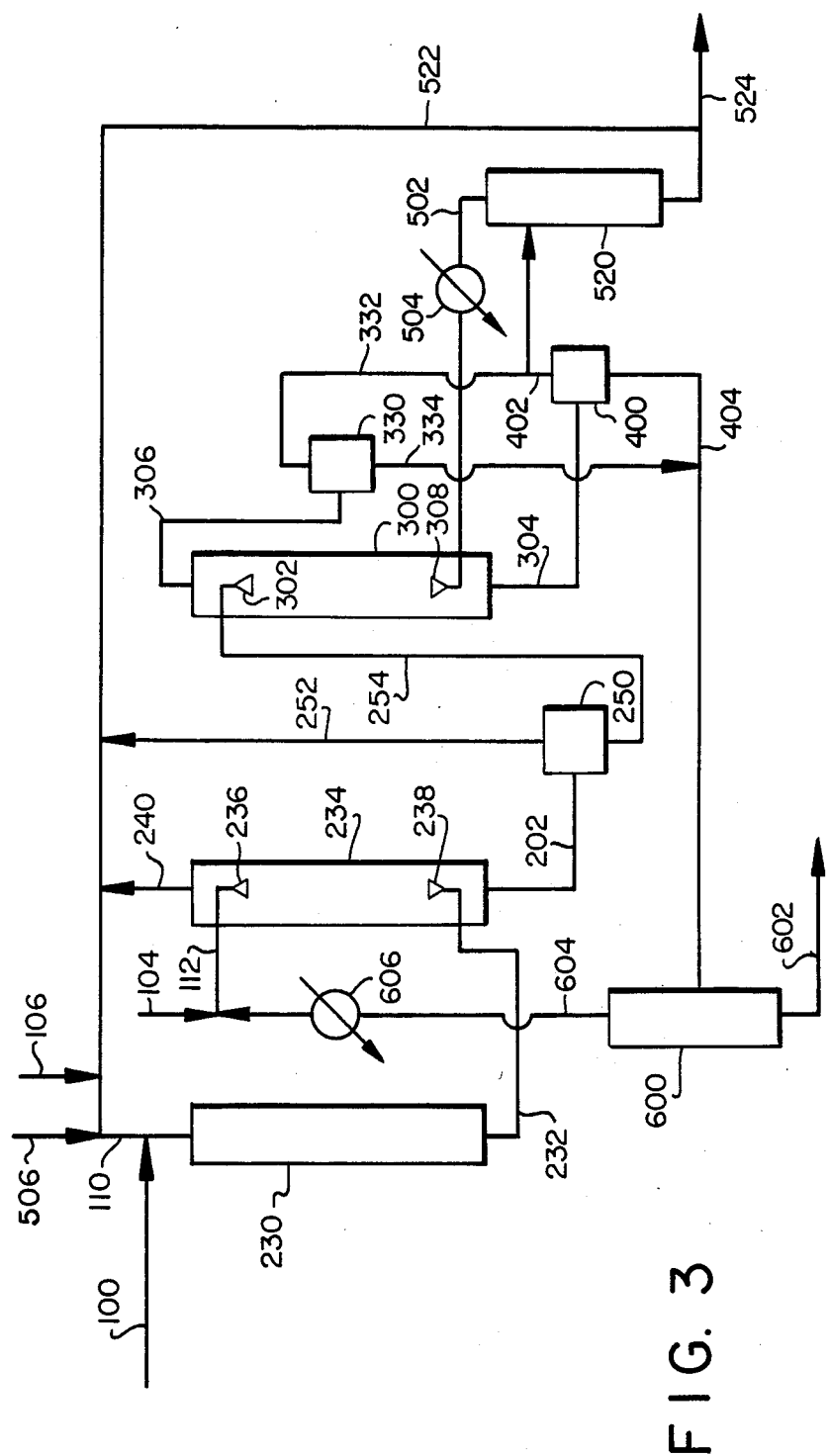
FIG. 3 is a schematic diagram of a process in accordance with this invention using a two-step hydrolysis reaction system.

FIG. 3 depicts a two-stage reaction system in which alkylene oxide via line 100 and organometalate-containing solvent via line 110 are introduced into downflow tubular reactor 320 to provide an associated moiety which is formed from the alkylene oxide and the organometalate. At the bottom of reactor 230 the associated moiety-containing product is removed via line 232 and is passed to countercurrent reactor 234 through distributor 238 located at a lower portion of the reactor. The solvent-containing phase is passed upwardly through reactor 234 and is contacted with water which is introduced via line 112 which is in communication with distributor 236 located at an upper portion of reactor 234. As with the reactor depicted in FIG. 2, zones are provided at each end of the reactor to further enable separation of the phases prior to leaving the reactor.

As depicted, the solvent-containing phase is withdrawn from reactor 234 via line 240 for return to reactor 230. In some instances, it may be desired to further separate any aqueous phase from the solvent-containing stream in line 240.

The aqueous phase that is withdrawn from reactor 234 via line 202 is passed to a phase separator 250 to recover additional solvent-containing phase. This additional solvent-containing phase is recycled to reactor 230 via line 252. The aqueous, alkylene glycol-containing phase from reactor 250 is passed via line 254 to the extraction vessel 300.

Because it is often desired to minimize the amount of water passing to reactor 230, the organometalate-rich solvent in line 306 from extraction vessel 300 is passed to phase separator 330 to enable additional aqueous, alkylene glycol-containing phase to be separated. This aqueous phase is passed via line 334 to line 404 for recovery of the alkylene glycol product in evaporator 600. The organometalate-rich solvent phase from separator 330 is passed via line 332 to flash evaporator 520 to provide an organometalate-lean solvent solution for use in extraction vessel 300.

Similar to the system depicted in FIG. 2, the make-up organometalate and water-immiscible solvent are provided to the solvent-containing stream passing to reactor 230.

Figure 4:
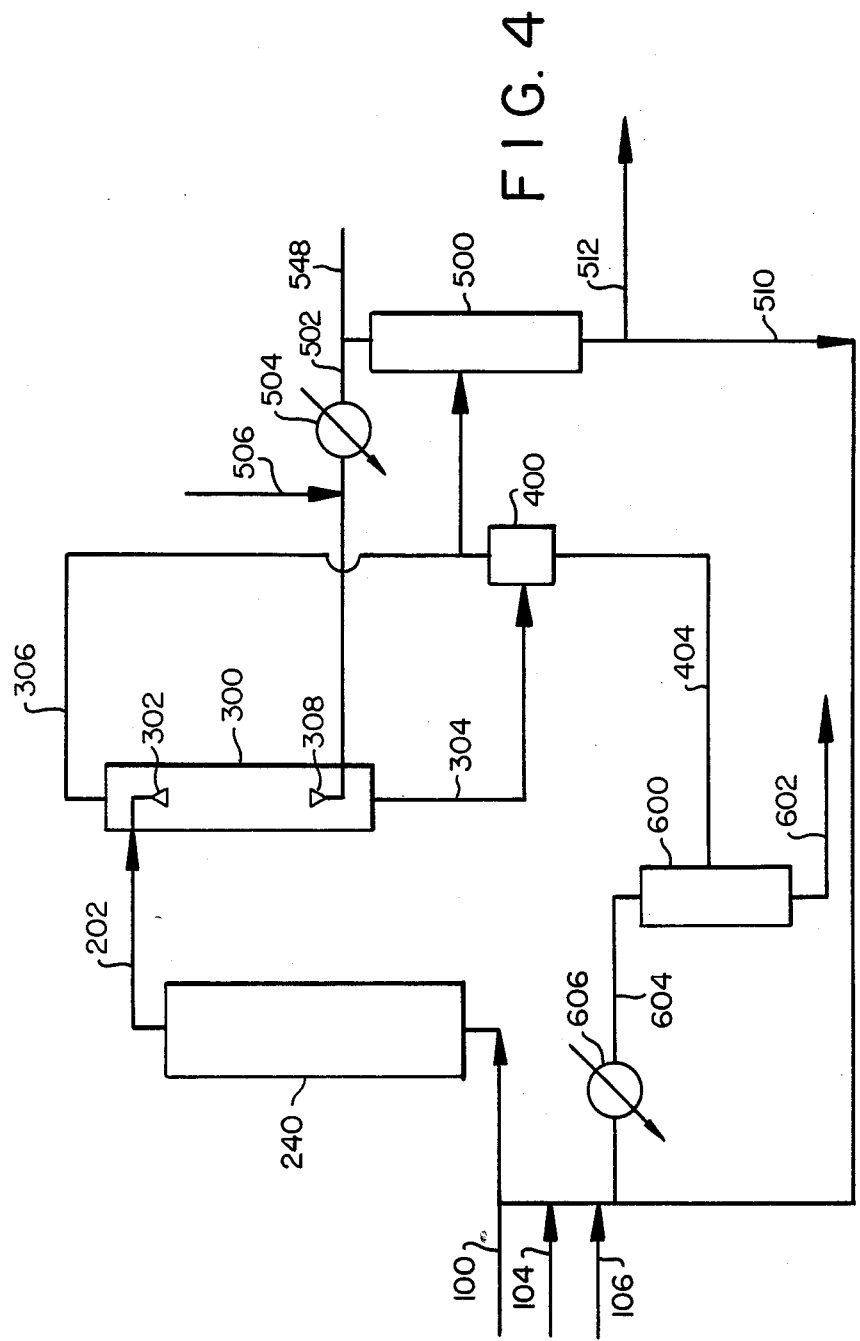
FIG. 4 is a schematic diagram of a process in accordance with this invention using a reaction zone containing metalate anion associated with a solid having electropositive complexing sites.

The system depicted in FIG. 4 employs an upflow reactor containing an anion exchange resin which has been exchanged with metalate anions. While numerous constructions of the reactor are possible, one method is to provide zones containing the anion exchange resin wherein each zone is separated by a screen to mitigate against crushing the exchange resin.

Although the primary metalate anion for enhancing the selectivity to monoalkylene glycol is fixed within reactor 240, organometalate added to the reactor via line 106 is intended to enhance the stability of the anion exchange resin. This is discussed further in copending U.S. patent application Ser. No. 14366, filed on even date herewith, of B. T. Keen, et al., herein incorporated by reference.

The purpose of the extraction is not only to recover organometalate that was added to enhance the stability of the anion exchange resin but also to recover degradation products of the anion exchange resin including metalate anion and possibly organic degradation products.

As depicted, line 548 is in communication with line 502 and serves to enable a purge to be taken from the overhead stream from distillation column 500 to prevent an undue build-up of organic products which may have occurred due to the degradation of the anion exchange resin.

The following is a specific illustration of a processes of this invention for purposes of facilitating understanding and is not intended to be in limitation thereof.

The apparatus comprises an isothermal reactor vessel (stainless steel) having an inside diameter of about 3.8 centimeters and length of about 150 centimeters. The effluent from the reactor vessel can be passed to a stainless steel, two liter capacity settling tank. The settling tank is provided with a line to draw off the predominently aqueous phase which passes to a four-stage mixer-settler extraction system. The mixer in each stage is about 250 cubic centimeters in capacity is provided and the settling section is 2 liters in capacity. The mixer-settlers are arranged in a counter-current configuration such that the predominently aqueous phase from the settling tank can be passed to the mixer section of the first mixer-settler and solvent extractant can be passed to the mixer section of the fourth mixer-settler. The aqueous phase from each settler can be passed to the mixer section of the next higher mixer-settler and the solvent-containing phase can be passed from the settler section of a mixer-settler to the mixer section of the next lower mixer-settler.

The solvent-containing phase in the settler section of the first mixer-settler can be combined with the solvent-containing phase of the settling tank and passed to a boiler (stainless steel, steam-heated having a volume of two liters). The overhead (solvent extractant) from the boiler can be passed through a water-cooled condenser into the mixer section of the fourth mixer-settler.

The aqueous phase from the settler section of the fourth mixer settler can be passed to an evaporator. The evaporator is a steam-jacketed stainless steel evaporator having a diameter of about 5 centimeters and length of about 180 centimeters. The overhead from the evaporator can be passed through a water-cooled condenser and recycled to a stainless steel mixing tank (about 4 liters in volume) adapted with an agitator having a rotation speed of about 400 rpm. The bottoms from the evaporator can be withdrawn into a holding tank (about 200 liter capacity steel drum).

In this illustration, ethylene oxide is continuously fed at a rate of about 19.3 grams per minute, at a temperature of about 20° to 22° C. into the feed tank at a pressure of about 42 atmospheres absolute and is admixed with about 7.2 grams per minute of deionized water (about 10° C.) and 72 grams per minute of recycle (about 85° C.) from the evaporator. The mixture is heated to about 140° C. and is passed to the top of the reactor which is maintained at a temperature of about 140° C.

The reaction product is withdrawn from the bottom of the reactor and passed to the settling tank. The settling tank is not insulated or heated and therefore some cooling of the stream occurs. The top phase (predominently aqueous) is passed to the first mixer-settler. The agitation in the mixer sections of each of the mixer-settlers is about 400 rpm.

The bottoms from the settling tank and the settler section of the first mixer-settler are passed to the boiler. The boiler is maintained at a temperature of about 85° C. and 5 atmospheres absolute. The overhead from the boiler is cooled to about 50° C. and introduced into the mixer section of the fourth mixer-settler.

The aqueous phase from the fourth mixer-settler is passed to the evaporator which is operated at a temperature of about 180° C. and 1.55 bars absolute. The bottoms from the evaporator are the alkylene glycol product, and the overhead is condensed by cooling to about 90° C. and is combined with the bottoms from the boiler and passed to the feed mixing tank.

The composition of the streams based on steady-state operation are set forth below:

| Feed to Reactor: | |
|---|---|
| Ethylene oxide, | 19.3 g/min |
| Water, | 35.8 g/min |
| Dichloromethane, | 42 g/min |
| BTHAM* | 27.2 g/min |
| Effluent from Reactor: | |
| Monoethylene glycol, | 23 g/min (86.4% selectivity) |
| Diethylene glycol, | 3.6 g/min |
| Water, | 28.5 g/min |
| BTHAM, | 27.2 g/min |
| Dichloromethane, | 42 g/min |
| Feed to First Mixer-Settler: | |
| Monoethylene glycol, | 23 g/min |
| Diethylene glycol, | 3.6 g/min |
| Water, | 28.4 g/min |
| BTHAM | 1.9 g/min |
| Dichloromethane, | less than 0.2 g/min |
| Solvent Phase from First Mixer-Settler: | |
| Dichloromethane, | 21. g/min |
| BTHAM, | about 1.9 g/min |
| Water, | less than 0.1 g/min |
| Aqueous Phase from Fourth Mixer-Settler: | |
| Monoethylene glycol, | 23 g/min |
| Diethylene glycol, | 3.6 g/min |
| Water, | 28.4 g/min |
| BTHAM, | less than 50 ppm by wt. |
| Dichloromethane, | less than 0.2 g/min |
| Feed to Boiler: | |
| Dichloromethane | 63 g/min |
| BTHAM, | 27.2 g/min |
| Water, | between 0.1 and 0.2 g/min |
| Overhead from Boiler | |
| Dichloromethane, | 21 g/min |
| Water | trace |
| Bottoms from Boiler: | |
| Dichloromethane | 42 g/min |
| BTHAM, | 27.2 g/min |
| Water, | between 0.1 and 0.2 g/min |
| Overhead from Evaporator | |
| Water | 28.4 g/min |

*BTHAM is bis[(tetra-n-hexyl)ammonium] molybdate.

We claim:

1. A continuous process for making alkylene glycols by the hydrolysis of alkylene oxide with water in the presence of selectivity-enhancing metalate anion-containing material comprising:

(a) providing alkylene oxide and water to a reaction zone containing selectivity-enhancing amounts of the metalate anion-containing material provided as an organometalate having an organic-containing cation and a metalate anion, said zone being maintained under conditions sufficient to form an aqueous solution of alkylene glycol, said aqueous solution also containing organometalate;

(b) withdrawing aqueous solution from the reaction zone and contacting at least a portion of the aqueous solution with a water-immiscible solvent in an extraction zone, in which solvent the organometalate is preferentially soluble as compared to water, to form an organometalate-rich solvent;

(c) separating the aqueous solution and the organometalate-rich solvent by phase separation to form an aqueous glycol-containing stream and a solvent-containing stream;

(d) separating at least a portion of the solvent-containing stream into an organometalate-lean stream containing water-immiscible solvent and into an organometalate-rich stream; and (e) introducing at least a portion of the organometalate-lean stream into the extraction zone to form at least a portion of the water-immiscible solvent and introducing at least a portion of the organometalate-rich stream into the reaction zone to form at least a portion of the organometalate therein.

2. The process of claim 1 wherein the aqueous glycol-containing stream is substantially free of water-immiscible solvent.

3. The process of claim 2 wherein the water-immiscible solvent has a normal boiling point below about 150° C. and the separation of the solvent-containing stream in step (d) is effected by vapor liquid separation under conditions of temperature, pressure and residence time such that the organometalate is not unduly adversely affected.

4. The process of claim 3 wherein the water-immiscible solvent has a normal boiling point below 100° C.

5. The process of claim 1 wherein the reaction zone contains water-immiscible solvent.

6. The process of claim 5 wherein the aqueous solution withdrawn from the reaction zone in step (b) contains water-immiscible solvent and the withdrawn solution is separated by phase separation into a solvent-rich phase and an aqueous phase wherein the aqueous phase is passed to the extraction zone.

7. The process of claim 6 wherein the solvent-rich phase is introduced into the reaction zone to provide at least a portion of the water-immiscible solvent content therein.

8. The process of claim 6 wherein the aqueous phase passed to the extraction zone contains less than about 1.0 weight percent organometalate.

9. The process of claim 8 wherein the water-immiscible solvent for contact with the aqueous solution in step (b) contains less than 0.5 weight percent organometalate.

10. The process of claim 1 wherein the extraction zone is at substantially the same pressure and temperature as the reaction zone.

11. The process of claim 3 wherein the water-immiscible solvent is the discontinuous phase in the extraction zone of step (b).

12. The process of claim 3 wherein the metalate anion has the formula $[(A)_qM(O)]^a$ where M is a polyvalent metal having a functional positive oxidation state; A represents one or more substituents to fill the remaining valencies (q) of M, and a is the negative charge of the anion.

13. The process of claim 12 wherein the metalate anion is selected from the group consisting of vanadate, molybdate and tungstate.

14. The process of claim 13 wherein the alkylene oxide has the formula

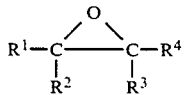

wherein each of $R^1$, $R^2$, $R^3$ and $R^4$ are the same or different and are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two or $R^1$, $R^2$, $R^3$ and $R^4$ having 3 to about 8 carbons.

15. The process of claim 14 wherein the alkylene oxide is ethylene oxide.

16. The process of claim 13 wherein the mole ratio of metalate anion to alkylene oxide is between about 0.1:100 to 1:1.

17. The process of claim 15 wherein the mole ratio of metalate anion to ethylene oxide is between about 0.1:100 to 1:1.

18. The process of claim 17 wherein the solvent comprises at least one member selected from the group consisting of benzene, toluene, xylene, dichloromethane and 1,1,2-trichloroethane.

19. The process of claim 13 wherein the organic-containing cation is represented by the formula $$[(R^0)_mY_n]^{x+}$$

wherein Y is a polyvalent element which is an ionic charge carrying center; $R^0$ is hydrogen or hydrocarbyl-containing substituent with the provision that Y has at least one $R^0$ which contains a hydrocarbyl substituent; m is the average number of electron pairs shaped by Y with the total $R^0$ groups; and n is the number of charge carrying centers, wherein m, n and x are related by the equation $x=n(V-m)$ in which V is the average functional oxidation state of Y wherein each electron pair used by each Y in bonding to R is given the value of 1 and the formal oxidation state of Y is the sum of the electron pairs bonding to $R^0$ and x/n, and x is an integer of 1 or 2.

20. The process of claim 19 wherein the organic-containing cation comprises an ammonium cation.

21. The process of claim 20 wherein the ammonium cation comprises a (tetraalkyl)ammonium cation.

22. The process of claim 19 wherein the organic-containing cation comprises phosphonium cation.

23. The process of claim 22 wherein the phosphonium cation comprises a tetraalkylphosphonium cation.

24. The process of claim 19 wherein the organic containing cation comprises a bis(trisubstituted phosphine)iminium cation.

* * * * *